(12) United States Patent
Sterner et al.

(10) Patent No.: US 10,045,553 B2
(45) Date of Patent: Aug. 14, 2018

(54) LEGUME/GRAIN BASED FOOD PRODUCT WITH PREBIOTIC/PROBIOTIC SOURCE

(71) Applicants: Mark H. Sterner, Riverside, CA (US); Mark M. Sterner, Sutherlin, OR (US); Deepa S. Deshmukh, Batavia, IL (US)

(72) Inventors: Mark H. Sterner, Riverside, CA (US); Mark M. Sterner, Sutherlin, OR (US); Deepa S. Deshmukh, Batavia, IL (US)

(73) Assignee: Mark H. Sterner, Riverside, CA (US)

( * ) Notice: Subject to any disclaimer, the term of this patent is extended or adjusted under 35 U.S.C. 154(b) by 0 days.

(21) Appl. No.: 14/971,821

(22) Filed: Dec. 16, 2015

(65) Prior Publication Data

US 2016/0175368 A1 Jun. 23, 2016

Related U.S. Application Data

(60) Provisional application No. 62/093,953, filed on Dec. 18, 2014.

(51) Int. Cl.
| | |
|---|---|
| *A61K 35/742* | (2015.01) |
| *A61K 36/48* | (2006.01) |
| *A23L 1/308* | (2006.01) |
| *A23L 11/00* | (2016.01) |
| *A23L 33/135* | (2016.01) |

(Continued)

(52) U.S. Cl.
CPC ............... *A23L 1/308* (2013.01); *A23L 7/10* (2016.08); *A23L 11/01* (2016.08); *A23L 33/135* (2016.08); *A23L 33/21* (2016.08); *A61K 36/48* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| 625,880 A | 5/1899 | Gere et al. |
| 665,323 A | 1/1901 | Gere et al. |
| (Continued) | | |

FOREIGN PATENT DOCUMENTS

| EP | 289060 | 2/1988 | |
| GB | 2163938 | 3/1986 | |
| WO | WO 2013082562 A1 * | 6/2013 | ......... A61K 31/7016 |

OTHER PUBLICATIONS

Anderson, James, W; et al; "Health benefits of dietary fiber" Nutrition Reviews, 67, 188-205, 2009.*

(Continued)

*Primary Examiner* — David W Berke-Schlessel
(74) *Attorney, Agent, or Firm* — Stetina Brunda Garred & Brucker

(57) ABSTRACT

A minimally processed ready-to-eat legume/grain product is provided containing a significant amount of prebiotic fiber and a probiotic source or is consumed with a probiotic source for the prevention and/or treatment of inflammatory chronic conditions such as inflammatory, autoimmune chronic conditions such as Irritable Bowel Syndrome (IBS), digestive disorders such chronic constipation, gastric acid reflux, diabetes, heart disease, obesity, some type of cancer, malabsorptive disorders, eczema as well mental health disorders such as anxiety disorder. The present invention is suitable for men and woman of all ages.

16 Claims, 2 Drawing Sheets

(51) Int. Cl.
*A23L 33/21* (2016.01)
*A23L 7/10* (2016.01)
*A61K 35/00* (2006.01)

(56) References Cited

U.S. PATENT DOCUMENTS

| | | |
|---|---|---|
| 707,646 A | 8/1902 | Scheele |
| 2,920,963 A | 1/1906 | Garzins |
| 1,063,208 A | 6/1913 | Norton |
| 1,071,312 A | 8/1913 | Greco |
| 1,088,741 A | 3/1914 | Stephens |
| 1,813,268 A | 7/1931 | Bachler |
| 2,019,141 A | 10/1935 | Knowles |
| 2,120,138 A | 6/1938 | Mathews et al. |
| 2,220,880 A | 11/1940 | Baer |
| 2,278,467 A | 4/1942 | Musher |
| 2,278,475 A | 4/1942 | Musher |
| 2,278,941 A | 4/1942 | Musher |
| 2,279,280 A | 4/1942 | Musher |
| 2,282,783 A | 5/1942 | Musher |
| 2,297,502 A | 9/1942 | Rudolph et al. |
| 2,343,149 A | 2/1944 | Krause, Jr. |
| 2,376,485 A | 5/1945 | Hermann et al. |
| 2,391,829 A | 11/1945 | Huber |
| 2,392,241 A | 1/1946 | Glabe |
| 2,402,675 A | 6/1946 | Shaffner |
| 2,456,073 A | 12/1948 | Newhouse |
| 2,475,554 A | 7/1949 | Moiler |
| 2,477,627 A | 8/1949 | Lanter |
| 2,587,372 A | 2/1952 | Oliver |
| 2,657,999 A | 11/1953 | Rauch |
| 2,873,663 A | 2/1959 | Hawk et al. |
| 2,996,385 A | 8/1961 | Weinecke et al. |
| 3,290,159 A | 12/1966 | Dorsey et al. |
| 3,291,615 A | 12/1966 | Thompson et al. |
| 3,415,664 A | 12/1968 | Montgomery et al. |
| 3,433,650 A | 3/1969 | Block et al. |
| 3,491,958 A | 1/1970 | Zucchini |
| 3,563,768 A | 2/1971 | Melnick |
| 3,617,309 A | 11/1971 | Rebane |
| 3,635,728 A | 1/1972 | Rockland et al. |
| 3,642,494 A | 2/1972 | Wagner |
| 3,650,763 A | 3/1972 | Touba |
| 3,652,294 A | 3/1972 | Marotta et al. |
| 3,661,071 A | 5/1972 | Toei et al. |
| 3,738,848 A | 6/1973 | Mader |
| 3,752,677 A | 8/1973 | Andrews et al. |
| 3,754,930 A | 8/1973 | Toei et al. |
| 3,800,050 A | 3/1974 | Popel |
| 3,800,056 A | 3/1974 | Mitchell, Jr. |
| 3,821,435 A | 6/1974 | Blake et al. |
| 3,869,556 A | 3/1975 | Rockland et al. |
| 3,881,033 A | 4/1975 | Steele |
| 3,983,261 A | 9/1976 | Mendoza |
| 3,987,207 A | 10/1976 | Spaeti et al. |
| 4,006,260 A | 2/1977 | Webb et al. |
| 4,060,645 A | 11/1977 | Risler et al. |
| 4,073,961 A | 2/1978 | Gasser et al. |
| 4,075,361 A | 2/1978 | Oberg |
| 4,152,974 A | 5/1979 | Tienor |
| 4,156,806 A | 5/1979 | Tiech et al. |
| 4,198,400 A | 4/1980 | Biegler |
| 4,251,558 A | 2/1981 | Kobayashi et al. |
| 4,267,199 A | 5/1981 | Koshida et al. |
| 4,335,584 A | 6/1982 | Lermuzeaux |
| 4,407,840 A | 10/1983 | Lathrop et al. |
| 4,409,250 A | 10/1983 | Van Hulle et al. |
| 4,415,599 A | 11/1983 | Bos |
| 4,450,180 A | 5/1984 | Watkins |
| 4,463,022 A | 7/1984 | Sterner et al. |
| 4,548,826 A | 10/1985 | Watkins |
| 4,585,660 A | 4/1986 | Sugisawa et al. |
| 4,676,990 A | 6/1987 | Huffman et al. |
| 4,691,374 A | 9/1987 | Watkins et al. |
| 4,717,578 A | 1/1988 | Biller et al. |
| 4,724,290 A | 2/1988 | Campbell |
| 4,735,816 A | 4/1988 | Sterner et al. |
| 4,737,376 A | 4/1988 | Brandlein et al. |
| 4,769,512 A | 9/1988 | Schulbach |
| 4,871,567 A | 10/1989 | Sterner et al. |
| 4,877,637 A | 10/1989 | Harp |
| 4,891,235 A | 1/1990 | Mizuguchi et al. |
| 4,900,578 A | 2/1990 | Bakker et al. |
| 4,990,348 A | 2/1991 | Spratt et al. |
| 5,044,777 A | 9/1991 | Watkins et al. |
| 5,079,027 A | 1/1992 | Wong et al. |
| 5,124,170 A | 6/1992 | Sterner et al. |
| 5,183,678 A | 2/1993 | Taga et al. |
| 5,213,831 A | 5/1993 | Leggott et al. |
| 5,232,732 A | 8/1993 | Harris et al. |
| 5,240,734 A | 8/1993 | Izzo et al. |
| 5,320,858 A | 6/1994 | Fazzolare et al. |
| 5,326,583 A | 7/1994 | Taga et al. |
| 5,366,748 A | 11/1994 | Villagran et al. |
| 5,366,754 A | 11/1994 | Rudan et al. |
| 5,372,826 A | 12/1994 | Holtz et al. |
| 5,409,729 A | 4/1995 | Richards et al. |
| 5,421,253 A | 6/1995 | Reymeyer et al. |
| 5,436,023 A | 7/1995 | Avera |
| 5,443,858 A | 8/1995 | Jensen et al. |
| 5,448,220 A | 9/1995 | Levy |
| 5,478,986 A | 12/1995 | Westerberg |
| 5,518,755 A | 5/1996 | Wong et al. |
| 5,681,607 A | 10/1997 | Maki et al. |
| 5,688,543 A | 11/1997 | Freeport et al. |
| 5,694,830 A | 12/1997 | Hodgson et al. |
| 5,714,193 A | 2/1998 | Fix et al. |
| 5,725,902 A | 3/1998 | Lesueur-Brymer et al. |
| 5,743,174 A | 4/1998 | Stickle |
| 5,744,188 A | 4/1998 | Kolla et al. |
| 5,750,166 A | 5/1998 | Shellhaass |
| 5,753,287 A | 5/1998 | Chedid et al. |
| 5,770,839 A | 6/1998 | Ruebush et al. |
| 5,863,592 A | 1/1999 | Sterner et al. |
| 5,948,954 A | 9/1999 | Horn et al. |
| 5,980,971 A | 11/1999 | Walsh |
| 5,996,480 A | 12/1999 | Kelley et al. |
| 6,040,503 A | 3/2000 | Ehlers et al. |
| 6,090,433 A | 7/2000 | Sterner et al. |
| 6,238,725 B1 | 5/2001 | Bush et al. |
| 6,355,291 B1 | 3/2002 | Rose et al. |
| 6,419,976 B1 | 7/2002 | Ehlers et al. |
| 6,465,031 B1 | 10/2002 | Bush et al. |
| 6,482,457 B1 | 11/2002 | Margolis |
| 6,602,534 B1 | 8/2003 | Rose et al. |
| 6,602,539 B2 | 8/2003 | Stubbs et al. |
| 6,808,732 B2 | 10/2004 | Boullin et al. |
| 6,837,682 B2 | 1/2005 | Evenson et al. |
| 6,953,574 B2 | 10/2005 | Sobol et al. |
| 7,029,716 B2 | 4/2006 | Margolis |
| 7,074,444 B2 | 7/2006 | Margolis |
| 7,087,262 B2 | 8/2006 | Nickels |
| 7,449,206 B2 | 11/2008 | Moser et al. |
| 7,740,894 B2 | 7/2010 | Squire et al. |
| RE41,885 E | 10/2010 | Margolis |
| 8,486,469 B2 | 7/2013 | Coleman et al. |
| 8,815,797 B2 | 8/2014 | Miner et al. |
| 2002/0136811 A1 | 9/2002 | Borders et al. |
| 2003/0068417 A1 | 4/2003 | Margolis |
| 2004/0137135 A1 | 7/2004 | Margolis |
| 2006/0153965 A1 | 7/2006 | Borders et al. |
| 2008/0171126 A1 | 7/2008 | Nelson et al. |
| 2008/0182007 A1 | 7/2008 | Barnett et al. |
| 2012/0315359 A1 | 12/2012 | Gandhi et al. |
| 2014/0193551 A1 | 7/2014 | Hoed |

OTHER PUBLICATIONS

Agil, Rania; et al; "Lentils enhance probiotic growth in yogurt and provide added benefit of antioxidant protection" LWT—Food Science and Technology, 40, 45-49, 2013.*

Beaudoin, Rachel; et al; "Improvement of Protein Quality of Whole Wheat" Experimental Biology and Medicine, 78, 450-451, 1951.*

(56) References Cited

OTHER PUBLICATIONS

Gourbeyre, Pascal; et al; "Probiotics, prebiotics, and synbiotics: impact on the gut immune system and allergic reactions" Journal of Leukocyte Biology, 89, 685-695, 2010.*
www.troop655.com; "Cooking Dinners"; Aug. 19, 2005; pp. 1-18.
www.tasteadventure.com; "Recipes"; Aug. 19, 2005; pp. 1-8.
Williams Sonoma; "Mexican"; May 24, 2005; p. 111.
www.wikipedia.org; "Refried Beans"; Mar. 29, 2006; pp. 1-2.
Zarela's Veracruz; "Vegetables and Side Dishes"; 2001; p. 285.
Wayne Gisslen; "Professional Cooking"; Third Edition; pp. 32-41.
Taste Adventure; "Instant Refried Beans"; 2 pgs.

\* cited by examiner

LEGUME/GRAIN BASED FOOD PRODUCT WITH PREBIOTIC/PROBIOTIC SOURCE

CROSS-REFERENCE TO RELATED APPLICATIONS

This present application claims priority to, and the benefit of, U.S. Provisional Application Ser. No. 62/093,953 entitled "LEGUME/GRAIN BASED FOOD PRODUCT WITH PREBIOTIC/PROBIOTIC SOURCE", filed on Dec. 18, 2014, the entire contents of which are expressly incorporated herein by reference.

STATEMENT RE: FEDERALLY SPONSORED RESEARCH/DEVELOPMENT

Not Applicable

BACKGROUND OF THE INVENTION

1. Technical Field

The present invention relates to a minimally processed ready-to-eat whole legume/grain based product containing significant amounts of prebiotic fiber and a probiotic source or is consumed with a probiotic source for the prevention and/or treatment of inflammatory, autoimmune chronic conditions such as irritable Bowel Syndrome (IBS), digestive disorders such chronic constipation, gastric acid reflux diabetes, heart disease, obesity, some type of cancer, malabsorptive disorders, eczema as well mental health disorders such as anxiety disorder.

The present invention is suitable for men and woman of all ages but in particularly those who are pregnant, breast feeding, young and growing children, elderly population, athletes, as well as those who have used or are using antibiotics, prescription and non-prescription drugs.

2. Description of the Related Art

The World Health Organization defines probiotic as "live micro-organisms which, when administered in adequate amounts, confer a health benefit on the host". Digestive or gut microbiota consists of tens of trillions of micro-organisms. The microbiota includes at least 1,000 different species of known bacteria with more than 3 million genes. Microbiota can weigh up to 2 kg of an individual's body weight. Such organisms are collectively referred to as probiotics.

The World Health Organization defines prebiotic fiber as "a selectively fermented ingredient that allows specific changes, both in the composition and/or activity in the gastrointestinal microflora that confers benefits upon the host's well-being and health". Essentially, prebiotic fiber acts as a food for probiotic micro-organisms and thus controls the growth of beneficial bacteria. The prebiotic fiber and probiotic micro-organisms have a synergistic relationship that is fundamental for the health of a user's digestive system and consequently for the maintenance of overall health.

The synergetic relationship between prebiotic fiber and probiotic microorganism is believed to be crucial to maintain the good health of a host.

Recent clinical studies have established the health promoting effects of probiotics which serve as a metabolic booster, enhance sports performance, are anti-inflammatory, promote antimicrobial activity, reduce gastrointestinal infections, improve lactose metabolism, exhibit antimutagenic and anticarcinogenic properties, enhance heart health, possess antidiarrheal properties, stimulate the immune system, alleviate inflammatory bowel disease, and suppress Heliobacterphylori infection. Additionally, probiotic-rich microflora has been shown to play an important role in the prevention and treatment of obesity, diabetes, and some cancers. These significant health benefits of probiotics have resulted in significant interest in the development and marketing of food products that contain probiotics. In addition, the demand for food and beverage products containing probiotics is anticipated to experience substantial growth in the future. Dietary sources and dietary forms of probiotics are numerous including but not limited to yogurt and yogurt drinks either cultured naturally or infused with a specific probiotic strain, fermented foods such as sauerkraut, kimchee or any other ready to eat forms including probiotic infused bars, cereals, snacks, and beverages. A variety of supplements, containing combinations of various probiotic strains are also available in the marketplace.

Clinical evidence indicates that a major factor to determine the functionality, growth, and viability of a diverse probiotic population is the ingestion of prebiotic fiber. In this regard, prebiotics have been found to play a significant role in promoting the various health benefits of probiotics. Basically, prebiotic fibers act as a food for probiotic microorganisms. Without prebiotics, probiotic flora will not flourish in the digestive tract of user. However, current prior art food products have failed to identify, promote, and address the beneficial relationship between prebiotic fiber and probiotic bacterial sources in a legume form.

The family of prebiotic fiber generally consists of Galactooligosaccharides (GOS) which includes Raffinose Family Oligosaccharides (RFO), sugar alcohols, and Fructan (which, in turn, includes fructooligosaccharides (FOS) and resistant starch (RS)). A common type of Fructan is Inulin which is found in natural plant products such as chicory root, Jerusalem artichoke, onion, garlic, and leek and, to a smaller extent, in wheat and wheat products. Recently, Inulin has been introduced in some food products to improve the texture and/or mouth feel of the product and, in some instances, to lower the fat content of the food product.

In contrast to Inulin, GOS, which includes RFO, sugar alcohols, and resistant starch, is found primarily in legumes and more particularly in various types of lentils and grains. In this regard, a quantity of 100 g of lentils can provide about 13 g of prebiotic fiber. The fiber concentration in legumes and grains can additionally be maximized through selective breeding and locational sourcing. In spite of this prebiotic fiber concentration, the prebiotic potential of legumes and grains has been substantially overlooked with only a few food products having been developed to utilize their prebiotic and nutritional potential.

As such, a substantial need in the art exists to develop and minimally processed legume/grain based product containing a significant amount of prebiotic fiber together with a probiotic source or designed to consumed with a probiotic source to improve user, health.

BRIEF SUMMARY OF THE INVENTION

The present invention specifically identifies and provides a functional food product having a symbiotic relationship between prebiotic fiber and probiotic bacteria and further identifies that the daily consumption of both prebiotic and probiotic sources is beneficial in the prevention and treatment of a variety of inflammatory chronic conditions such as IBS, diabetes, heart disease, obesity, and eczema among others. Further, the daily consumption of probiotic and prebiotic sources has been found to reduce the impact of typical side effects caused by use of antibiotics and intake of highly processed food ingredients in one's daily diet.

The present invention provides a functional food product (i.e., a food product derived from a whole food source) and includes prebiotic fibers which are believed to be essential for the growth and survival of probiotic microorganisms. Various natural sources for such prebiotics are utilized such as legumes and grains which are high in GOS and which contains RFO, RS and Fructan. Similarly, natural sources of chicory root, agave, onion, garlic and Jerusalem artichoke may be utilized which are rich in FOS. Further, botanical/biological, pharmaceutical and/or nutraceutical ingredients can be added preferably in powder, granular or extract form. The resultant legume/grain based functional food product of the present invention therefore utilizes legumes and grains either alone or in combination as the major ingredient to provide a substantial amount of total prebiotic fiber to aid in probiotic digestion.

The present invention contemplates the manufacture of the legume and/or grain based product via processes that minimize nutrient loss during cooking and dehydration. The present invention additionally contemplates infusion or enrobing of the legume/grain product with various additives such as botanical, pharmaceutical and/or nutraceutical ingredients including, but not limited to, chicory root based Inulin, anti-inflammatory turmeric and/or one or more probiotic strains. The resultant food product provides a minimally processed, ready-to-eat, instant legume/grain based functional food product that contains a significant amount of *lactobacillus* coagulants, chicory based Inulin, and total fiber, a significant portion of which is prebiotic fiber.

BRIEF DESCRIPTION OF THE DRAWINGS

These and other features and advantages of the various embodiments disclosed herein will be better understood with respect to the following descriptions and drawings, in which like number refer to like parts throughout, and in which.

DETAILED DESCRIPTION OF THE INVENTION

The detailed description set forth below is intended as a description of the presently preferred embodiments of the invention, and is not intended to represent the only form in which the present invention may developed or utilized. It is to be understood, however, that the same or equivalent functions may be accomplished by different embodiments that are also intended to be encompassed within the spirit and scope of the present invention. It is further understood that use of relational terms such as first, second, and the like are used solely to distinguish one from another entity without necessarily requiring implying any actual such relationship or order between such entities.

The present invention preferably provides a minimally processed, ready-to-eat, legume/grain based fu food product containing a significant amount of prebiotic fiber and preferably a probiotic source or which is designed to be consumed with a probiotic source for the prevention and/or treatment of inflammatory chronic conditions such as IBS, diabetes, heart disease, obesity, and eczema. For purposes of this patent application, the terms "minimally processed" and/or "minimal processing" will be defined in accordance with USDA standards, namely, minimal processing means the product was processed in a manner that does not fundamentally alter the product. In this regard, the Applicants believe that superior nutritional benefits are obtained by utilizing whole natural legume/grain products in the manufacturing process as opposed to extracts of legume/grain products. However, both minimally processed whole natural legume/gram products and/or legume/grain product extracts are contemplated herein.

For purposes of this invention, probiotics will be defined as live microorganisms which when administered in adequate amounts, confer a health benefit on a user. Prebiotics will be defined as non-digestible substances that provide a beneficial physiological effect on a user by selectively stimulating the favorable growth or activity of a limited number of indigenous probiotic bacteria. Legumes shall be defined as alseeds grown in a pod including, but not limited to, lentils, peas, beans, and peanuts.

Figure 1:
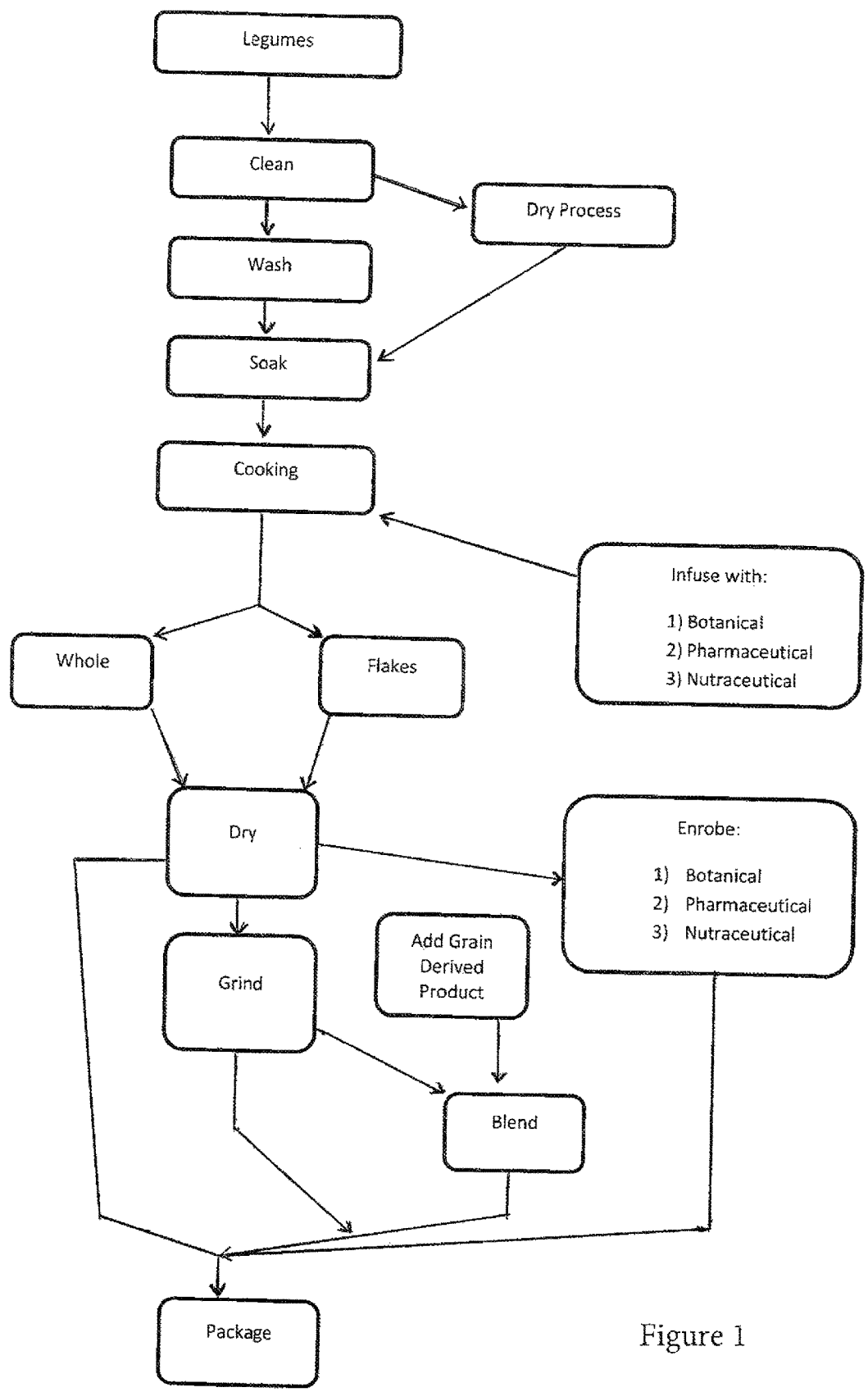
FIG. 1 is a flow diagram of a preferred method of producing the legume/grain based food product with a prebiotic/probiotic source of the present invention derived primarily from legume products.

The legume/grain based food product with prebiotic/probiotic sources of the present invention derived primarily from legume based product is illustrated in FIG. 1. By way of example and not limitation, a preferred legume source comprises lentils. However, all legumes are contemplated herein. As shown in FIG. 1, the legumes are cleaned by conventional techniques are then either washed in a water, bath or stream or washed in a conventional dry process. Subsequently, the legumes are soaked to hydrate the legume. Preferably, the legumes are then cooked and dehydrated by a process that minimizes nutrient loss. Preferred cooking and dehydration processes are disclosed n U.S. Pat. No. 4,735,816 entitled "Dehydrated Refried Bean Product and Methods of Manufacture" and U.S. Pat. No. 6,090,433 entitled "Leguminous Snack Food and Process of Making the Same", both of which are commonly owned by the assignee of the subject application, the disclosures of which are expressly incorporated herein by reference. The '816 cooking and dehydration process form the cooked legume into a flake configuration. The product of the '433 cooking and dehydration processing leave the legume essentially whole form. However, those having ordinary skill in the art will recognize that other conventional cooking and dehydration processes to produce whole legumes are expressly contemplated herein including but not limited to pressure cooking, puffing, infra-red cooking, and atmospheric steaming.

As shown in FIG. 1, during the cooking process, the legumes may be infused with either botanical, pharmaceutical and/or nutraceutical ingredients. Such infused ingredients can be in either powder, granular or extract form. By way of example and not limitation, such ingredients may include carotenoids such as beta carotene, lutein, zeaxanthin and/or lycopin. Additional ingredients may include dietary fiber including, but not limited to, insoluble fiber, soluble fiber, beta glucan, inulin, prebiotic and/or probiotic compounds. Other exemplary ingredients include, fatty acids such as monounsaturated fatty acid, polyunsaturated fatty acids, Omega 3 fatty acids, conjugated linoleic acid and medium chain fatty acids. Flavonoids such as anthocyanins, flavanols, procyanidins, proanthocyanidins, flavanones and flavonols including quercetin and sulforaphane are additionally contemplated herein. In addition, minerals such as calcium, magnesium, potassium and selenium as well as phenolic acids including caffeic acid and ferulic acid can be utilized as added ingredients. Further, plant stencils, phytoestrogens including, but not limited to, isoflavones and lignans as well as sulphides and sulthiols and water and fat soluble vitamins are contemplated herein.

After cooking, with or without the infusion of botanical, pharmaceutical and nutraceutical ingredients, the whole and/or flaked legumes are subjected to a conventional drying process to reduce their moisture content. Conventional drying processes such as air drying, oven drying and/or sun drying are contemplated herein. After drying, the legumes can be enrobed in various conventional ways such as coating, dipping or spraying processes with the same or similar botanical, pharmaceutical and/or nutraceutical ingredients defined in relation to the above-referenced infusion process.

Although not by way of limitation, the applicant has found that the infusion and/or enrobing steps preferably include a common type of fructan found abundantly in chicory root, Jerusalem artichoke, onion, garlic and leek and in smaller quantities in wheat and wheat products. The applicant has additionally found that preferred additive for infusion or enrobing of the legume product includes turmeric which is a powerful antioxidant, antimicrobial, anti-cancerous, and anti-inflammatory compound. Those skilled in the art, however, will recognize, that other known antioxidants and anti-inflammatory compounds such as By way of example and not limitation, such ingredients may include carotenoids such as beta carotene, lutein, zeaxanthin and/or lycopin. Additional ingredients may include dietary fiber including, but not limited to, insoluble fiber, soluble fiber, beta glucan inulin, prebiotic and/or probiotic compounds. Other exemplary ingredients include fatty acids such as monounsaturated fatty acid, polyunsaturated fatty acids, Omega 3 fatty acids, conjugated linoleic acid and medium chain fatty acids. Flavonoids such as anthocyanins, flavanols, procyanidins, proanthocyanidins, flavanones and flavonols including quercetin and sulforaphane are additionally contemplated herein. In addition, minerals such as calcium, magnesium, potassium and selenium as well as phenolic acids including caffeic acid and ferulic acid can be utilized as added ingredients. Further, plant stenols, phytoestrogens including, but not limited to, isoflavones and lignans as well as sulphides and sulthiols and water and fat soluble vitamins are contemplated herein. Further, the applicant has found that the addition of recent probiotic strain compounds which have been developed to enhance the effects of prebiotics are contemplated during the enrobing step. By way of example and not limitation, one of such probiotic strains is the ganedenBC30 probiotic strain manufactured by Ganeden Biotech and Schiff Nutrition, the disclosure of which is expressly incorporated herein by reference. However, those having skill in the art will recognize that other probiotic strains are contemplated herein. The resultant enrobed legume product may then be packaged as shown in FIG. 1. Alternatively, the resultant dried legume product can be packaged or be ground via conventional techniques into either a powder, granulated or nugget form prior to packaging.

Figure 2:
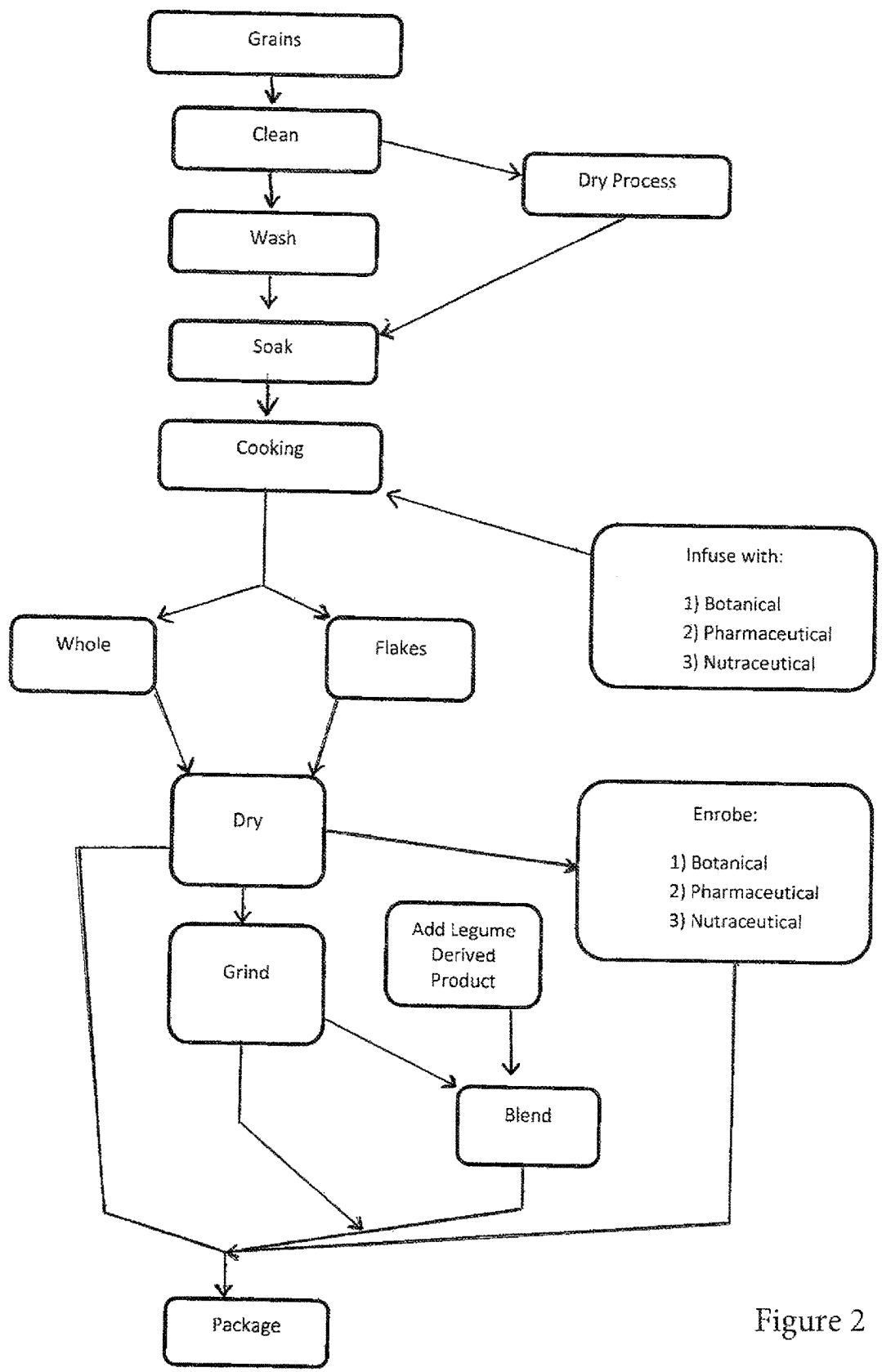
FIG. 2 is a flow diagram legume/grain based food product with prebiotic/probiotic source of the present invention derived primarily from grains.

Referring to FIG. 2, a preferred process for forming the legume/grain based food product with probiotic/prebiotic source derive primarily from grains is illustrated. Although all grains are contemplated herein, preferred grain candidates include rice, oats, barley, quinoa, corn wheat, millet, and buckwheat. As with the legumes, the grains are cleaned and subjected either to a dry process or washing process and are subsequently soaked to hydrated the same. Conventional cooking techniques may then be employed which may or may not include an infusion of the botanical, pharmaceutical and/or nutraceutical ingredients previously recited in relation to the legume process, the whole or flaked grains may then be dried utilizing conventional techniques.

After drying, the grains may be enrobed with the same or similar botanical, pharmaceutical and nutraceutical ingredients referred to in relation the legume process and proceed to packaging. Alternatively, the dried grains may be packaged or subjected to a grinding process which forms the grains into a powder or granulated or nugget configuration. The ground product may then be packaged for later consumption.

Although both the legume based product illustrated in FIG. 1 and the grain based product illustrated in FIG. 2 can be packaged and consumed individually, the present invention additionally contemplates the mixing and/or blending of the legume derived product with the grain derived product in blending steps shown in both FIGS. 1 and 2. Depending upon desired constituency, the percentage of blending between legume derived and grain derived products can be varied.

The legume/grain based food product of the present invention can be used in a variety of dietary applications such as baby food, breakfast foods, snack items, as an ingredient in soups, stews, salads, smoothie mixes and as a ready-to-eat meal. A preferred dietary use is as an additive or topping for conventional probiotic source foods such as yogurt. As is well known, yogurt comprises a natural probiotic source and by combining the use of the legume/grain based prebiotic food product of the present invention, the symbiotic effect of the prebiotic and probiotic relationship established. Those skilled in the art will cognize, however, that the legume/grain based prebiotic food product of the present invention can additionally be utilized in all conventional food product preparations.

The applicant has found that by adding a 2 ounce quantity of the legume derived (lentil) prebiotic functional food product of the present invention to a conventional sized serving of yogurt, the protein count increased by as much as 18 percent per single serving with additional increases in micronutrients such as iron, folate, potassium, and soluble and nonsoluble fiber. Further, the prebiotic fiber contained in the legume derived (lentil) prebiotic food product of the present invention serves as a food for probiotic bacteria consumed in the form of yogurt and supplements. Those skilled in the art will recognize that the legume/grain based food product with prebiotic/probiotic source of the present invention is suitable for consumers across their lifespan ranging from prenatal state to beyond. The prebiotic and probiotic containing legume/grain product of the present invention is believed to be advantageous to those who are suffering from the most digestive tract related disorders such ulcerative colitis, IBS, gas, bloating, and constipation, inflammatory, autoimmune chronic conditions such IBS, digestive disorders such chronic constipation, gastric acid reflux, diabetes, heart disease, obesity, some type of cancer, malabsorptive disorders, eczema as well mental health disorders such as anxiety disorder.

The present invention is suitable for men and woman of all ages and may be utilized throughout their lifetime ranging from the prenatal stage to beyond.

The particular embodiment shown and described herein are by way of example and for purposes of illustrative discussion of the embodiments of the present invention only and are presented in the cause of providing what is believed to be the most, useful and readily understood description of the principles and conceptual aspects of the present invention. In this regard, no attempt is made to show more details as is necessary for a fundamental understanding of the disclosure, the description disclosed herein making apparent to those skilled in the art how the several embodiments of the presently disclosed invention may be embodied in practice.

What is claimed is:

1. A method for producing an enriched dried whole leguminous food product, the method comprising the steps of:
   a) hydrating a quantity of whole legumes to a moisture content of between 52% to 55% by weight;
   b) cooking the whole legumes;
   c) dehydrating the whole legumes to a moisture content of between 6% to 8% by weight;
   d) enrobing the external surface of the whole legumes with a prebiotic fiber and a probiotic strain, the prebiotic fiber being chosen being from the group consisting of: chicory-derived inulin, Jerusalem artichoke-derived inulin, onion-derived inulin, garlic-derived inulin, or combinations thereof, the probiotic strain comprising a lactic acid-forming bacterial species chosen from the genus *Bacillus*, the genus *Lacrtobacillus*, or a combination thereof.

2. The method of claim 1, wherein the prebiotic fiber is chicory-derived inulin.

3. The method of claim 1, wherein the probiotic strain comprises *Bacillus coagulans*.

4. The method of claim 1, wherein the hydrating step is performed by soaking the quantity of legumes in water at a temperature of about 212 degrees fahrenheit.

5. The method of claim 1, wherein the cooking step is performed by submerging the legumes in boiling water at a pressure higher than ambient.

6. The method of claim 1, wherein the cooking step is performed by disposing the legumes in a rotating vessel and heating the legumes in a pressurized steam environment.

7. The method of claim 1, wherein the quantity of legumes are chosen from: pinto beans, pink beans, red beans, black beans, navy beans, black eye beans, kidney beans, garbanzo beans, lentils, peas, and combinations thereof.

8. The method of claim 1, wherein the enrobing step occurs subsequent to the cooking step and prior to the drying step.

9. The method of claim 1, wherein the enrobing step occurs subsequent to the drying step.

10. An enriched dried whole leguminous food product, wherein the enriched dried whole leguminous food product is produced by a process comprising the steps of:
    a) providing a quantity of whole uncooked legumes;
    a) hydrating the quantity of whole uncooked legumes to a moisture content of between 52% to 55% by weight;
    b) cooking the whole legumes;
    c) dehydrating the whole legumes to a moisture content of between 6% to 8% by weight;
    d) enrobing the external surface of the whole legumes with a prebiotic fiber and a probiotic strain, the prebiotic fiber being chosen being from the group consisting of: chicory-derived inulin, Jerusalem artichoke-derived inulin, onion-derived inulin, garlic-derived inulin, wheat-derived inulin, or combinations thereof, the probiotic strain comprising a lactic acid-forming bacterial species chosen from the genus *Bacillus*, the genus *Lactobacillus*, or a combination thereof.

11. The enriched dried whole leguminous food product of claim 10, wherein during the process for its production, the prebiotic fiber chosen is chicory-derived inulin.

12. A dried whole leguminous food product, the dried leguminous food product comprising:
    a dried, cooked whole legume:
    a prebiotic fiber enrobed upon the external surface of the dried, cooked whole legume; and
    a probiotic strain enrobed on the external surface of the dried, cooked whole legume;
    wherein the prebiotic fiber is chosen from the group consisting of: chicory-derived inulin, Jerusalem artichoke-derived inulin, onion-derived inulin, garlic-derived inulin, or combinations thereof; and
    wherein the probiotic strain is a lactic acid-forming bacterial species chosen from the genus *Bacillus*, the genus *Lactobacillus*, or a combination thereof.

13. The dried whole leguminous food product of claim 12, wherein during the process for its production, the prebiotic fiber chosen is chicory-derived inulin.

14. The method of claim 1, wherein the step of enrobing the external surface of the whole legumes is performed via a process chosen from: coating, dipping, spraying, or combinations thereof.

15. The enriched dried whole leguminous food product of claim 10, wherein in the process for its production, the step of enrobing the external surface of the whole legumes is performed via a process chosen from: coating, dipping, spraying, or combinations thereof.

16. The dried whole leguminous food product of claim 1, wherein the prebiotic fiber and the probiotic strain are enrobed upon external surface of the whole legume via a process chosen from: coating, dipping, spraying, or combinations thereof.

* * * * *